United States Patent [19]

Schönafinger et al.

[11] Patent Number: 4,558,058

[45] Date of Patent: Dec. 10, 1985

[54] SUBSTITUTED 1,4-DIHYDROPYRIDINES AND THEIR USE AS MEDICAMENTS

[75] Inventors: Karl Schönafinger, Alzenau; Helmut Bohn; Melitta Just, both of Schöneck; Piero Martorana, Bad Homburg, all of Fed. Rep. of Germany

[73] Assignee: Cassella Aktiengesellschaft, Frankfurt, Fed. Rep. of Germany

[21] Appl. No.: 560,197

[22] Filed: Dec. 9, 1983

[30] Foreign Application Priority Data

Dec. 20, 1982 [DE] Fed. Rep. of Germany ....... 3247118

[51] Int. Cl.$^4$ .................... C07D 413/04; A61K 31/44
[52] U.S. Cl. ................................. 514/342; 546/277; 546/256; 546/257; 546/258; 546/280; 514/340; 514/333
[58] Field of Search ................ 546/277; 424/266, 263; 514/342, 340, 333

[56] References Cited

U.S. PATENT DOCUMENTS

| 4,144,343 | 3/1979 | Baldwin | 424/263 |
| 4,145,432 | 3/1979 | Sato | 546/277 |
| 4,260,765 | 4/1981 | Harrison | 546/280 |
| 4,414,213 | 11/1983 | Poindexter | 424/248.5 |

FOREIGN PATENT DOCUMENTS

| 0042089 | 12/1981 | European Pat. Off. |
| 1963186 | 6/1971 | Fed. Rep. of Germany |
| 2005116 | 9/1971 | Fed. Rep. of Germany |
| 2747513 | 5/1979 | Fed. Rep. of Germany |
| 2847236 | 5/1980 | Fed. Rep. of Germany |
| 1271302 | 4/1972 | United Kingdom |

OTHER PUBLICATIONS

Chemical Abstracts, vol. 93, No. 23, 220596j, 12/8/80, (Bayer).
Chemical Abstracts, vol. 94, No. 11, 83961d, 3/16/81, (Institute of Organic Synthesis).

Primary Examiner—Jane T. Fan
Attorney, Agent, or Firm—Berman Aisenberg & Platt

[57] ABSTRACT 1,4-dihydropyridines of the formula I

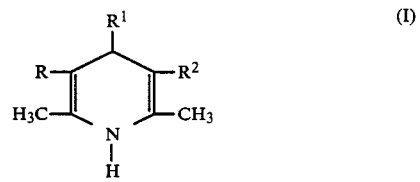

in which R denotes, for example, —$CO_2R^3$ or cyano, $R^1$ denotes, for example, an optionally substituted phenyl, pyridyl or thienyl, $R^2$ denotes the radical of a 5-membered, optionally substituted, ring having at least one double bond and at least 2 heteroatoms or heteroatom groups from the series comprising O, N, NH and S, and $R^3$ denotes, for example, alkyl or alkoxyalkyl, and their acid addition salts, have valuable pharmacological properties.

26 Claims, No Drawings

SUBSTITUTED 1,4-DIHYDROPYRIDINES AND THEIR USE AS MEDICAMENTS

The invention relates to new substituted 1,4-dihydropyridines of the formula I

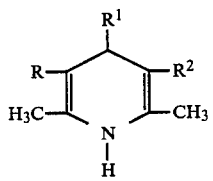

in which R denotes —$CO_2R^3$, cyano or one of the meanings indicated under $R^2$, $R^1$ denotes pyridyl or thienyl or phenyl, the pyridyl or thienyl or phenyl radical optionally having 1 or 2 identical or different substituents from the group comprising alkyl having 1 to 4C atoms, alkoxy having 1 to 4C atoms, halogen, trifluoromethyl, nitro or cyano, $R^2$ denotes the radical of a 5-membered ring having one double bond or two double bonds and 2, 3 or 4 heteroatoms or heteroatom groups from the series comprising O, N, NH, S, at least one of the hetero atoms or hetero atom groups being an N atom, the 5-membered ring optionally having 1 or 2 identical or different substituents from the group comprising alkyl having 1 to 4C atoms, alkylthio having 1 to 4C atoms, aralkyl having a total of 7 to 9C atoms, alkoxyalkyl having a total of 2 to 5C atoms, cycloalkyl having 5 or 6C atoms, aminocarbonylmethylthio, methoxycarbonyl, ethoxycarbonyl or phenyl, $R^3$ denotes alkyl having 1 to 6C atoms, alkoxyalkyl having 3 to 8C atoms, dialkylaminoalkyl having a total of 4 to 9C atoms, N-aralkyl-N-alkylaminoalkyl having a total of from 10 to 14C atoms or cycloalkyl having 5 or 6C atoms, and their acid-addition salts.

The invention also relates to a process for the preparation of the compounds of the formula I and to their use as medicaments.

The radicals alkyl and alkoxy which are mentioned are, even when they are combined together or in other radicals, such as, for example, alkoxyalkyl, aralkyl, dialkylaminoalkyl or alkoxycarbonyl, or as substituents for other radicals, straight-chain or branched. Where ranges for the numbers of carbons in them or in the groups containing them have not already been indicated above, they normally contain 1 to 4C atoms.

The aralkyl radicals mentioned are, in particular, phenalkyl radicals, namely phenylpropyl, phenylethyl or benzyl, of which phenylethyl and, in particular, benzyl are preferred.

As a rule, halogen denotes chlorine, bromine or fluorine, preferably chlorine or bromine, and very particularly preferably chlorine.

In particular, R denotes one of the meanings indicated under $R^2$, such as, for example, oxadiazolyl, in particular 1,3,4-oxadiazol-2-yl or 3-benzyl-1,2,4-oxadiazol-5-yl. R preferably denotes —$CO_2R^3$.

$R^1$ can be a 2-, 3- or 4-pyridyl radical or a 2- or 3-thienyl radical, it being possible for these radicals to have one or two identical or different substituents.

$R^1$ preferably denotes phenyl which optionally has one or two identical or different substituents, preferably from the series comprising chlorine, bromine, fluorine, nitro, cyan, methyl, methoxy and trifluoromethyl. Examples of radicals of this type which are represented by $R^1$ are: phenyl, 2-chlorophenyl, 3-chlorophenyl, 4-chlorophenyl, 2,3-dichlorophenyl, 2-nitrophenyl, 3-nitrophenyl, 3-cyanophenyl, 3-methoxyphenyl, 3-trifluoromethylphenyl, 2-trifluoromethylphenyl, o-tolyl, m-tolyl or and p-tolyl.

$R^1$ particularly preferably denotes a phenyl which is monosubstituted by cyano, nitro or chlorine or disubstituted by chlorine, the substituents preferably being located in the 2- and/or 3-position of the phenyl nucleus. $R^1$ very particularly preferably denotes 2-nitrophenyl, 3-nitrophenyl, 3-cyanophenyl, 2-chlorophenyl and 2,3-dichlorophenyl.

$R^2$ can, for example, be an oxazolyl, thiazolyl, imidazolyl, triazolyl, tetrazolyl, oxadiazolyl or thiadiazolyl radical. Examples of suitable substituents for the radicals $R^2$ are: methyl, ethyl, n-propyl, i-propyl, n-butyl, i-butyl, tert.-butyl, benzyl, methylthio, i-propylthio, methoxymethyl, 2-methoxyethyl, aminocarbonylmethylthio, methoxycarbonyl, ethoxycarbonyl, cyclopentyl, cyclohexyl and phenyl. Those of the radicals of 5-membered rings which are represented by $R^2$ and which contain two nitrogen atoms and one oxygen atom and two double bonds, such as, for example, 1,3,4-oxadiazol-2-yl, 1,2,4-oxadiazol-5-yl and 1,2,4-oxadiazol-3-yl are preferred. Preferred substituents are: methyl, ethyl, i-propyl, tert.-butyl, benzyl, methylthio, i-propylthio, aminocarbonylmethylthio and methoxymethyl. Particularly preferred substituents are: methyl, ethyl and benzyl. 1,3,4-oxadiazol-2-yl, 5-methyl-1,3,4-oxadiazol-2-yl, 5-ethyl-1,3,4-oxadiazol-2-yl, 3-methyl-1,2,4-oxadiazol-5-yl, 3-ethyl-1,2,4-oxadiazol-5-yl and 3-benzyl-1,2,4-oxadiazol-5-yl are particularly preferred for $R^2$.

In the N-aralkyl-N-alkylaminoalkyl radical represented by $R^3$, the N-aralkyl-N-alkylamino group is located, in particular, on the terminal C atom of the alkyl radical, such as, for example: 2-(N-benzyl-N-methylamino)ethyl, 2-(N-phenethyl-N-methylamino)ethyl and 2-(N-benzyl-N-ethylamino)ethyl.

$R^3$ preferably denotes alkyl having 1 to 5C atoms, alkoxyalkyl having 1 to 4C atoms in the alkoxy moiety and 2 to 4C atoms in the alkyl moiety, dialkylaminoalkyl having a total of 3 to 6C atoms, it being possible for each of the alkyl groups substituting the amino group to have 1 to 3C atoms, and the alkoxy group in the alkoxyalkyl radical and the dialkylamino group in the dialkylaminoalkyl radical particularly being located on the terminal C atom of the alkyl radical. Examples of preferred radicals $R^3$ of this type are: methyl, ethyl, n-propyl, i-propyl, n-butyl, i-butyl, sec.-butyl, tert.-butyl, neopentyl, 2-methoxyethyl, 2-i-propoxyethyl, 2-n-butoxyethyl, 3-methoxy-n-propyl and 2-dimethylaminoethyl. $R^3$ very particularly preferably denotes methyl, n-propyl, i-propyl, n-butyl, i-butyl, tert.-butyl, 2-methoxyethyl and 2-i-propoxyethyl.

Those compounds of the formula I in which the radicals have one or, in particular, several of the indicated preferred meanings are preferred. Those compounds in which the radicals have one or, in particular, several, and preferably all, of the indicated particularly preferred meanings are very particularly preferred.

Examples of particularly preferred compounds of the formula I are the compounds in the Examples 1z, 2b, 2r, 2s, 2v and, in particular, 2n and 2z2 which follow.

The substituted 1,4-dihydropyridines of the formula I can be prepared, in analogy to the preparation of other 1,4-dihydropyridine compounds, starting from compounds of the formulae II to IX

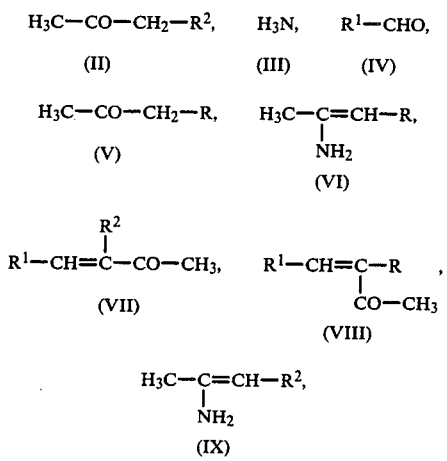

by reacting together
(a)
  2 mol of a compound of the formula II and
  1 mol of a compound of the formula IV and
  1 mol of a compound of the formula III or
(b)
  1 mol of a compound of the formula II and
  1 mol of a compound of the formula III and
  1 mol of a compound of the formula IV and
  1 mol of a compound of the formula V or
(c)
  1 mol of a compound of the formula II and
  1 mol of a compound of the formula IV and
  1 mol of a compound of the formula VI or
(d)
  1 mol of a compound of the formula VI and
  1 mol of a compound of the formula VII or
(e)
  1 mol of a compound of the formula VIII and
  1 mol of a compound of the formula II and
  1 mol of a compound of the formula III or
(f)
  1 mol of a compound of the formula V and
  1 mol of a compound of the formula III and
  1 mol of a compound of the formula VII or
(g)
  1 mol of a compound of the formula VIII and
  1 mol of a compound of the formula IX or
(h)
  2 mol of a compound of the formula IX and
  1 mol of a compound of the formula IV or
(i) 1 mol of a compound of the formula V and
  1 mol of a compound of the formula IV and
  1 mol of a compound of the formula IX or
(k)
  1 mol of a compound of the formula VII and
  1 mol of a compound of the formula IX
and, if desired, converting the resulting compound in a manner known per se into an acid addition salt.

However, starting from the compounds of the formulae II to IX, there are other possible processes for the synthesis of the compounds of the formula I. The variants of the process are variants or part steps of the known Hantzsch synthesis of pyridines.

For all variants (a) to (k) the reaction is carried out at room temperature (20° C.) or, in particular, at elevated temperature, for example in a range from 20° to 120° C. For all variants (a) to (k) the reaction is preferably carried out at the reflux temperature of the solvent or solvent mixture used. Normally, the reaction is carried out under atmospheric pressure, but it can also be carried out under a pressure differing from atmospheric pressure.

The reactions are carried out in water or an inert organic solvent. Examples of suitable solvents are alcohols, in particular those having 1 to 6C atoms, such as, for example, methanol, ethanol, i- and n-propanol, i-, sec.- and tert.-butanol, n-, i-, sec.-, tert.-pentanol, n-hexanol, cyclopentanol and cyclohexanol; ethers, in particular those having 2 to 8C atoms in the molecule, such as, for example, diethyl ether, methyl ethyl ether, di-n-propyl ether, diisopropyl ether, methyl n-butyl ether, ethyl propyl ether, dibutyl ether and tetrahydrofuran; 1,4-dioxane, 1,2-dimethoxyethane and bis-$\beta$-methoxyethyl ether; polyethers, such as, for example, polyethylene glycols having a molecular weight up to about 600; oligoethylene glycol dimethyl ethers, such as, for example, pentaglyme; glycols and partially etherified glycols, such as, for example, ethylene glycol, propylene glycol, trimethylene glycol, ethylene glycol monomethyl ether, ethylene glycol monoethyl ether and diethylene glycol monoethyl ether; ketones, in particular those having 3 to 10C atoms in the molecule, such as, for example, acetone, methyl ethyl ketone, methyl n-propyl ketone, diethyl ketone, 2-hexanone, 3-hexanone, di-n-propyl ketone, diisopropyl ketone, diisobutyl ketone, cyclopentanone, cyclohexanone, benzophenone and acetophenone; aliphatic hydrocarbons, such as, for example, low-boiling and high-boiling petroleum ethers; aromatic hydrocarbons, such as, for example, benzene, toluene, o-, m- and p-xylene; pyridine; halogenated aliphatic or aromatic hydrocarbons, such as, for example, methylene chloride, chloroform, carbon tetrachloride, ethylene chloride, chlorobenzene and dichlorobenzene; nitriles, such as, for example, acetonitrile; amides, such as, for example, dimethylformamide and N-methylpyrrolidone; hexamethylphosphoric triamides; sulphoxides, such as, for example, dimethyl sulphoxide; water. It is also possible to use mixtures of various solvents. Alcohols or mixtures of alcohols with water are preferred as a rule.

Of the abovementioned process variants for the preparation of the compounds of the formula I, process variant (c) is preferred.

The starting materials of the formula II to IX which are required for the preparation of the compounds of the formula I are known or can readily be prepared by the processes known for the particular class of compounds. The enamino compounds of the formulae VI and IX can, where they are not already known, be prepared by, for example, the method of A. C. Cope, J. Amer. chem. Soc. 67, 1017 (1945).

The following may be mentioned as examples of enamino compounds of the formulae VI and IX: methyl 3-aminocrotonate, ethyl 3-aminocrotonate, propyl 3-aminocrotonate, i-propyl 3-aminocrotonate, n-propyl 3-aminocrotonate, 2-methoxyethyl 3-aminocrotonate, 3-methoxypropyl 3-aminocrotonate, 2-butoxyethyl 3-aminocrotonate, 2-butoxyethyl 3-aminocrotonate, cyclopentyl 3-aminocrotonate, cyclohexyl 3-aminocrotonate, 2-(2-aminopropen-1-yl)-4-methyl-5-ethoxycarbonylthiazole, 2-(2-aminopropen-1-yl)thiazole, 2-(2-aminopropen-1-yl)-4-phenylthiazole, 5-(2-aminopropen-1-yl)-3-methyl-1,2,4-oxadiazole, 5-(2-aminopropen-1-yl)-3-ethyl-1,2,4-oxadiazole, 5-(2-aminopropen-1-yl)-3-tert.-butyl-1,2,4-oxadiazole, 5-(2-aminopropen-1-yl)-

3-benzyl-1,2,4-oxadiazole, 2-(2-aminopropen-1-yl)-1,3,4-oxadiazole, 2-(2-aminopropen-1-yl)-5-(aminocarbonylmethylthio)-1,3,4-oxadiazole, 2-(2-aminopropen-1-yl)-5-methyl-1,3,4-oxadiazole, 3-(2-aminopropen-1-yl)-1,2,4-oxadiazole, 3-(2-aminopropen-1-yl)-5-methyl-1,2,4-oxadiazole, 3-(2-aminopropen-1-yl)-5-benzyl-1,2,4-oxadiazole, 5-(2-aminopropen-1-yl)-1,2,4-thiadiazole and 5-(2-aminopropen-1-yl)-3-methylthio-1,2,4-thiadiazole.

The aldehydes of the formula IV serving as starting compounds can, where they are not already known, be prepared by, for example, the methods described by E. Mosettig, Org. Reactions VIII, 218 ff. (1954). Examples of suitable aldehydes of the formula IV are: benzaldehyde, 2-, 3- or 4-methylbenzaldehyde, 2-, 3- or 4-ethylbenzaldehyde, 2-, 3- or 4-i-propylbenzaldehyde, 2-, 3- or 4-tert.-butylbenzaldehyde, 2-, 3- or 4-methoxybenzaldehyde, 2-, 3- or 4-i-propoxybenzaldehyde, 2-, 3- or 4-bromobenzaldehyde, 2-, 3- or 4-chlorobenzaldehyde, 2-, 3- or 4-fluorobenzaldehyde, 2-, 3- or 4-cyanobenzaldehyde, 2-, 3- or 4-trifluoromethylbenzaldehyde, 2-, 3- or 4-nitrobenzaldehyde, 2,4- or 2,6-dimethylbenzaldehyde, 2,4- or 2,6-dichlorobenzaldehyde, 2,4- or 2,6-dibromobenzaldehyde, 2,4- or 2,6-dinitrobenzaldehyde, 2,4- or 2,6-diethylbenzaldehyde, 3-chloro-4-trifluoromethylbenzaldehyde, 3-methyl-4-trifluoromethylbenzaldehyde, 3-methoxy-4-chlorobenzaldehyde, 2-methyl-4-cyanobenzaldehyde, pyridine-2-aldehyde, pyridine-3-aldehyde, pyridine-4-aldehyde, 4-methylpyridine-2-aldehyde, 5-methylpyridine-2-aldehyde, 6-methylpyridine-2-aldehyde, thiophene-2-aldehyde, thiophene-3-aldehyde, 5-nitrothiophene-2-aldehyde, 5-methylthiophene-2-aldehyde, 5-chlorothiophene-2-aldehyde and 5-methoxythiophene-2-aldehyde.

The derivatives of acetoacetic ester required as starting compounds of the formula V can, where they are not already known, be prepared by the processes described in Houben-Weyl, Methoden der Organischen Chemie (Methods of Organic Chemistry) VII/4, (1968), 230 ff. and by H. O. House and S. K. Larson, J. Org. Chem. 33, (1968), 61.

Examples of suitable starting compounds of the formula V are cyanoacetone, methyl acetoacetate, ethyl acetoacetate, i-propyl acetoacetate, tert.-butyl acetoacetate, n-hexyl acetoacetate, neopentyl acetoacetate, cyclohexyl acetoacetate, 2-(di-methylamino) ethyl acetoacetate and 3-(diethylamino)propyl acetoacetate.

The ylidene compounds of the formulae VII and VIII which are required as starting components can, where they are not already known, be prepared by the method in Org. Reactions XV, 204 ff, (1967).

Examples of suitable starting compounds of the formulae VII and VIII are: methyl 2-benzylideneacetoacetate, cyclopentyl 2-benzylideneacetoacetate, ethyl 2-(2-, 3- or 4-bromobenzylidene)acetoacetate, i-propyl 2-(2-, 3- or 4-nitrobenzylidene)acetoacetate, sec.-butyl 2-(2-, 3- or 4-tri-fluoromethylbenzylidene)acetoacetate, neopentyl 2-(2-, 3- or 4-ethylbenzylidene)acetoacetate, 2-ethoxyethyl 2-(2-, 3- or 4-tert.-butylbenzylidene)acetoacetate, butyl 2-(2-, 3- or 4-propoxybenz-ylidene)acetoacetate, hexyl 2-(2-, 3- or 4-chlorobenzylidene)-acetoacetate, methyl 2-(2-, 3- or 4-dichlorobenzylidene)aceto-acetate and i-propyl 2-(3-methyl-4-cyanobenzylidene)acetoacetate.

The compounds of the formula II can, where they are not already known, be prepared by the process described in Monatshefte für Chemie 113, 781 ff. (1982). Examples of suitable starting compounds of the formula II are 5-acetonyl-1,2,4-oxadiazole, 3-methyl-5-acetyl-1,2,4-oxadiazole, 3-ethyl-5-acetyl-1,2,4-oxadiazole, 3-tert.-butyl-5-acetyl-1,2,4-oxadiazole, 3-methylthio-5-acetyl-1,2,4-oxadiazole, 3-benzyl-5-acetyl-1,2,4-oxadiazole, 2-acetonyl-1,3,4-oxadiazole, 5-methyl-2-acetonyl-1,3,4-oxadiazole, 5-i-propyl-2-acetonyl-1,3,4-oxadiazole, 3-acetonyl-1,2,4-oxadiazole, 5-ethyl-3-acetonyl-1,2,4-oxadiazole, 5-ethylthio-3-acetonyl-1,2,4-oxadiazole, 5-phenethyl-3-acetonyl-1,2,4-oxadiazole, 5-acetonyl-1,2,4-thiadiazole, 3-ethyl-5-acetonyl-1,2,4-thiadiazole and 3-benzyl-5-acetonyl-1,2,4-thiadiazole.

When the 1,4-dihydropyridine derivatives of the formula I have basic substituents, they form acid addition salts with inorganic or organic acids. Inorganic or organic acids are suitable for the formation of acid addition salts of these types. Examples of suitable acids are: hydrogen chloride, hydrogen bromide, naphthalenedisulphonic acids, in particular naphthalene-1,5-disulphonic acid, phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, isonicotinic, methanesulphonic, p-toluenesulphonic, citric or adipic acid. Pharmacologically acceptable acid addition salts are preferred. The acid addition salts are prepared as is customary by mixing the components, advantageously in a suitable solvent or diluent. In the synthesis of the compounds of the formula I, it is possible for the acid addition salts to be produced first in the course of work-up. The free compounds of the general formula I can, where required, be obtained from the acid addition salts in a known manner, for example by dissolving or suspending in water and making alkaline, for example with sodium hydroxide solution, and then isolating.

Compounds of the formula I having different meanings for R and $R^2$ have an asymmetric carbon atom in the 4-position of the dihydropyridine ring. Thus these compounds occur as the racemate and in the form of the optically active enantiomers. In the case where the compounds of the formula I have more than one asymmetric atom, diastereomers and their mixtures also occur. Mixtures of diastereomers and racemic mixtures of enantiomers can be separated into the individual components by known processes. For example, mixtures of diastereomers can be separated into the diastereomers by fractional recrystallisation or using chromatographic processes. A racemate can be converted by, for example, reaction with a suitable enantiomeric compound into a mixture of diastereomeric salts which is then separated into the individual diastereomeric salts by, for example, fractional recrystallisation. The diastereomeric salts are then cleaved in a known manner to give the enantiomeric compounds.

It has already been disclosed that certain 1,4-dihydropyridines have interesting pharmacological properties (F. Bossert, W. Vater "Due Naturwissenschaften" 58, 578, (1971). As a rule, the known active compounds are 1,4-dihydropyridine-3,5-dicarboxylic esters.

It has now been found, surprisingly, that the new compounds of the formula I according to the invention which do not contain two ester groups have particularly interesting cardiovascular effects. Since they are highly effective calcium antagonists, they inhibit the contraction induced by calcium in the muscle cell and have a hypotensive and antianginal action, and can thus contribute to, for example, lowering the blood pressure and relieving the load on the heart. Thus, the compounds according to the invention can be employed, inter alia, for high blood pressure and angina pectoris, and thus are an enrichment of pharmacy.

The compounds of the formula I and their pharmacologically acceptable acid addition salts can thus be administered alone, in mixtures with one another or in the form of pharmaceutical formulations which allow enteral or parenteral use and which contain, as the active constituent, an effective dose of at least one compound of the formula I or one of its acid addition salts together with customary pharmaceutically acceptable vehicles and additives, to humans as medicaments. The formulations normally contain about 0.5 to 90% by weight of the therapeutically active compound.

It is possible to administer the medicaments orally, for example in the form of pills, uncoated, lacquered or coated tablets, granules, hard and soft gelatin capsules, solutions, syrups, emulsions or suspensions, or aerosol mixtures. However, it is also possible to administer them rectally, for example in the form of suppositories, or parenterally, for example in the form of solutions for injection, or percutaneously, for example in the form of ointments or tinctures.

The pharmaceutical products are prepared in a manner known per se, pharmaceutically inert inorganic or organic vehicles being used. For the preparation of pills, uncoated and coated tablets and hard gelatin capsules, for example, lactose, maize starch or derivatives thereof, talc, stearic acid or its salts, etc., can be used. Examples of vehicles for soft gelatin capsules and suppositories are fats, waxes, semi-solid and liquid polyols, natural or hardened oils, etc. Examples of suitable vehicles for the preparation of solutions and syrups are water, sucrose, invert sugar, glucose, polyols, etc. Examples of suitable vehicles for the preparation of solutions for injection are water, alcohols, glycerol, polyols, vegetable oils, etc.

The pharmaceutical products can, in addition to the active compounds and vehicles, also contain additives, such as, for example, fillers, extenders, disintegrants, binders, lubricants, wetting agents, stabilisers, emulsifiers, preservatives, sweeteners, colorants, flavourings and aromas, thickening agents, diluents, buffer substances and solvents or solubilisers or agents for achieving a depot effect, as well as salt for modifying the osmotic pressure, coating agents or antioxidants. They can also contain two or more compounds of the formula I and/or their pharmacologically acceptable acid addition salts as well as other therapeutically active compounds.

Examples of relevant additional therapeutically active substances are: β-receptor blockers, such as, for example, propranolol, pindolol and metoprolol; antianginal agents, such as, for example, carbocromen or molsidomine; tranquillizers, such as, for example, barbituric acid derivatives, 1,4-benzodiazepines and meprabamate; diuretics, such as, for example, chlorothiazide; agents improving the tonicity of the heart, such as, for example, digitalis products; hypotensive agents, such as, for example, hydralazine, dihydralazine and prazosin; clonidine, rauwolfia alkaloids; agents which lower the level of fatty acids in the blood, such as, for example, bezafibrate, fenofibrate; agents for the prophylaxis of thrombosis, such as, for example, phenprocoumon.

The compounds of the formula I, their pharmacologically acceptable acid addition salts and pharmaceutical products which contain the compounds of the formula I or their pharmacologically acceptable acid addition salts as the active compound can be used in humans for controlling or preventing disorders which are brought about by an inflow of calcium into muscle cells and which can be controlled by administering calcium antagonists. Thus, for example, they can be employed as an anti-hypertensive medicament for the various forms of high blood pressure, for controlling or preventing angina pectoris, etc., and for treating disturbances of cerebral and peripheral blood flow. The dosage can be varied within wide limits and should be adjusted to suit the individual situation in each particular case. In general, a daily dose of about 0.01 to 10 mg/kg, preferably 0.05 to 5 mg/kg, of body weight is suitable for achieving effective results on oral administration. The daily dose with intravenous administration is generally about 0.001 to 10 mg/kg, preferably 0.01 to 5 mg/kg, of body weight. The daily dose is normally divided into several, for example, 2, 3 or 4, part administrations, particularly when relatively large amounts are administered. Where appropriate, it can be necessary, depending on the individual response, to use less or more than the daily dose indicated.

EXAMPLE 1

Methyl 1,4-dihydro-2,6-dimethyl-4-(3-nitrophenyl)-5-(3-methyl-1,2,4-oxadiazole-5-yl)pyridine-3-carboxylate 3.02 g of 3-nitrobenzaldehyde, 2.3 g of methyl aminocrotonate and 2.8 g of 3-methyl-5-acetonyl-1,2,4-oxadiazole in 30 ml of isopropanol are heated to boiling for 5 hours. After allowing the mixture to cool, the precipitated solid is filtered off with suction and recrystallised from ethanol. Melting point=239° to 240° C. Yield: 3.8 g

| Analysis: | C | H | N | O |
|---|---|---|---|---|
| Calculated: | 58.4 | 4.9 | 15.1 | 21.6 |
| Found: | 58.6 | 4.9 | 15.3 | 21.1 |

The following are prepared in an analogous manner:
(a) Methyl 1,4-dihydro-2,6-dimethyl-4-(2,3-dichlorophenyl)-5-(3-methyl-1,2,4-oxadiazol-5-yl)pyridine-3-carboxylate, melting point=252° to 254° C.;
(b) 2-Methoxyethyl 1,4-dihydro-2,6-dimethyl-4-(3-nitrophenyl)-5-(3-methyl-1,2,4-oxadiazol-5-yl)pyridine-3-carboxylate, melting point=214° to 216° C.;
(c) Methyl 1,4-dihydro-2,6-dimethyl-4-(2-nitrophenyl)-5-(3-methyl-1,2,4-oxadiazol-5-yl)pyridine-3-carboxylate, melting point=220° to 222° C.;
(d) 2-Methoxyethyl 1,4-dihydro-2,6-dimethyl-4-(2,3-dichlorophenyl)-5-(3-methyl-1,2,4-oxadiazol-5-yl)pyridine-3-carboxylate, melting point=196° to 199° C.;
(e) Methyl 1,4-dihydro-2,6-dimethyl-4-(3-pyridyl)-5-(3-methyl-1,2,4-oxadiazol-5-yl)pyridine-3-carboxylate, melting point=248° to 250° C.;
(f) Methyl 1,4-dihydro-2,6-dimethyl-4-phenyl-5-(3-methyl-1,2,4-oxadiazol-5-yl)pyridine-3-carboxylate, melting point=198° to 200° C.;
(g) 2-Methoxyethyl 1,4-dihydro-2,6-dimethyl-4-(2-nitrophenyl)-5-(3-methyl-1,2,4-oxadiazol-5-yl)pyridine-3-carboxylate, melting point=177° to 180° C.;
(h) Methyl 1,4-dihydro-2,6-dimethyl-4-(3-methoxyphenyl)-5-(3-ethyl-1,2,4-oxadiazol-5-yl)pyridine-3-carboxylate, melting point=180° to 183° C.;

(j) Methyl 1,4-dihydro-2,6-dimethyl-4-(3-nitrophenyl)-5-(3-tert.-butyl-1,2,4-oxadiazol-5-yl)pyridine-3-carboxylate, melting point=197° to 199° C.;

(k) Methyl 1,4-dihydro-2,6-dimethyl-4-(2-chlorophenyl)-5-(3-methyl-1,2,4-oxadiazol-5-yl)pyridine-3-carboxylate, melting point=211° to 213° C.;

(l) Methyl 1,4-dihydro-2,6-dimethyl-4-(3-chlorophenyl)-5-(3-methyl-1,2,4-oxadiazol-5-yl)pyridine-3-carboxylate, melting point=228° to 230° C.;

(m) Methyl 1,4-dihydro-2,6-dimethyl-4-(4-chlorophenyl)-5-(3-methyl-1,2,4-oxadiazol-5-yl)pyridine-3-carboxylate, melting point=227° to 229° C.;

(n) 3-Methoxypropyl 1,4-dihydro-2,6-dimethyl-4-phenyl-5-(3-isopropyl-1,2,4-oxadiazol-5-yl)pyridine-3-carboxylate, melting point=194° to 196° C.;

(o) 2-Butoxyethyl 1,4-dihydro-2,6-dimethyl-4-(2,3-dichlorophenyl)-5-(tert.-butyl-1,2,4-oxadiazol-5-yl)pyridine-3-carboxylate, melting point=211° to 213° C.;

(p) 2-Dimethylaminoethyl 1,4-dihydro-2,6-dimethyl-4-(3-trifluoromethylphenyl)-5-(3-benzyl-1,2,4-oxadiazol-5-yl)pyridine-3-carboxylate, melting point=205° to 207° C.;

(q) 2-Dimethylaminoethyl 1,4-dihydro-2,6-dimethyl-4-(2,3-dichlorophenyl)-5-(3-methyl-1,2,4-oxadiazol-5-yl)pyridine-3-carboxylate, melting point=170° to 172° C.;

(r) 2-Isopropoxyethyl 1,4-dihydro-2,3-dimethyl-4-(2,3-dichlorophenyl)-5-(3-methyl-1,2,4-oxadiazol-5-yl)pyridine-3-carboxylate, melting point=147° to 149° C.;

(s) Butyl 1,4-dihydro-2,6-dimethyl-4-(2,3-dichlorophenyl)-5-(3-methyl-1,2,4-oxadiazol-5-yl)pyridine-3-carboxylate, melting point=221° to 223° C.;

(t) 2-Methylethyl 1,4-dihydro-2,6-dimethyl-4-(3-cyanophenyl)-5-(3-methyl-1,2,4-oxadiazol-5-yl)pyridine-3-carboxylate, melting point=175° to 178° C.;

(u) 2-Methoxyethyl 1,4-dihydro-2,6-dimethyl-4-(2,3-dimethoxyphenyl)-5-(3-methyl-1,2,4-oxadiazol-5-yl)pyridine-3-carboxylate, melting point=165° to 167° C.;

(v) Isopropyl 1,4-dihydro-2,6-dimethyl-4-(2,3-dichlorophenyl)-5-(3-methyl-1,2,4-oxadiazol-5-yl)pyridine-3-carboxylate, melting point=194° to 196° C.;

(w) Isobutyl 1,4-dihydro-2,6-dimethyl-4-(2,3-dichlorophenyl)-5-(3-methyl-1,2,4-oxadiazol-5-yl)pyridine-3-carboxylate, melting point=158° to 159° C.;

(x) 2-Methoxyethyl 1,4-dihydro-2,6-dimethyl-4-(3-chlorophenyl)-5-(3-methyl-1,2,4-oxadiazol-5-yl)pyridine-3-carboxylate, melting point=183° to 187° C.;

(y) 2-Methoxyethyl 1,4-dihydro-2,6-dimethyl-4-(2,3-dimethoxyphenyl)-5-(1,3,4-oxadiazol-2-yl)pyridine-3-carboxylate, melting point=205° to 207° C.;

(z) Isobutyl 1,4-dihydro-2,6-dimethyl-4-(3-nitrophenyl)-5-(1,3,4-oxadiazol-2-yl)pyridine-3-carboxylate, melting point=213° to 215° C.;

(z1) Methyl 1,4-dihydro-2,6-dimethyl-4-(3-nitrophenyl)-5-(2-aminocarbonylmethylthio-1,3,4-oxadiazol-5-yl)pyridine-3-carboxylate, melting point=246° to 248° C.;

(z2) Methyl 1,4-dihydro-2,6-dimethyl-4-(2,3-dichlorophenyl)-5-(2-aminocarbonylmethylthio-1,3,4-oxadiazol-5-yl)pyridine-3-carboxylate, melting point=216° to 218° C.

EXAMPLE 1A

2-Dimethylaminoethyl 1,4-dihydro-2,6-dimethyl-(2,3-dichlorophenyl)-5-(3-methyl-1,2,4-oxadiazol-5-yl) pyridine-3-carboxylate-hydrochloride.

5 g of the compound of Example 1q are dissolved in hot isopropanol. 5 ml of a saturated methanolic hydrochloric acid solution are cautiously added to the hot solution. The mixture is allowed to cool to room temperature with stirring and stirring is continued for a further hour. The precipitation is filtered off with suction. Melting point=225° C.

| Analysis | C | H | N | O | Cl |
|---|---|---|---|---|---|
| Calculated | 51.7 | 5.1 | 11.5 | 9.8 | 21.8 |
| Found | 51.5 | 5.3 | 11.3 | 9.9 | 21.9 |

EXAMPLE 2

2-Methoxyethyl 1,4-dihydro-2,6-dimethyl-4-(3-nitrophenyl)-5-(1,3,4-oxadiazol-2-yl)pyridine-3-carboxylate 3.02 g of 3-nitrobenzaldehyde, 3.18 g of 2-methoxyethyl aminocrotonate and 2.52 g of 2-acetonyl-1,3,4-oxadiazole in 30 ml of ethanol are heated to boiling for 5 hours. After allowing to cool down, the solid is filtered off with suction and recrystallised from ethyl acetate. 2.3 g of solid are obtained after a second recrystallisation from ethanol. Melting point=208° C.

| Analysis: | C | H | N | O |
|---|---|---|---|---|
| Calculated: | 57.0 | 5.0 | 14.0 | 24.0 |
| Found: | 56.7 | 5.2 | 14.3 | 23.8 |

The following are prepared in a similar manner:

(a) Methyl 1,4-dihydro-2,6-dimethyl-4-(3-nitrophenyl)-5-(1,3,4-oxadiazol-2-yl)pyridine-3-carboxylate, melting point=266° to 268° C.;

(b) Methyl 1,4-dihydro-2,6-dimethyl-4-(2,3-dichlorophenyl)-5-(1,3,4-oxadiazol-2-yl)pyridine-3-carboxylate, melting point=260° to 262° C.;

(c) Methyl 1,4-dihydro-2,6-dimethyl-4-(3-nitrophenyl)-5-(5-methyl-1,3,4-oxadiazol-2-yl)pyridine-3-carboxylate, melting point=267° to 269° C.;

(d) 2-Methoxyethyl 1,4-dihydro-2,6-dimethyl-4-(3-nitrophenyl)-5-(5-methyl-1,3,4-oxadiazol-2-yl)pyridine-3-carboxylate, melting point=234° to 236° C.;

(e) Methyl 1,4-dihydro-2,6-dimethyl-4-(2,3-dichlorophenyl)-5-(5-methyl-1,3,4-oxadiazol-2-yl)pyridine-3-carboxylate, melting point=238° to 240° C.;

(f) Methyl 1,4-dihydro-2,6-dimethyl-4-(3-trifluoromethylphenyl)-5-(5-methyl-1,3,4-oxadiazol-2-yl)pyridine-3-carboxylate, melting point=207° to 208° C.;

(g) Methyl 1,4-dihydro-2,6-dimethyl-4-(2-chlorophenyl)-5-(5-methyl-1,2,4-oxadiazol-3-yl)pyridine-3-carboxylate, melting point=214° to 216° C.;

(h) Isopropyl 1,4-dihydro-2,6-dimethyl-4-(3-methoxyphenyl)-5-(5-methyl-1,2,4-oxadiazol-3-yl)pyridine-3-carboxylate, melting point=180° to 182° C,;

(i) Ethyl 1,4-dihydro-2,6-dimethyl-4-(3-methylphenyl)-5-(5-methoxymethyl-1,2,4-oxadiazol-3-yl)pyridine-3-carboxylate, melting point=165° to 168° C.;

(k) Isobutyl 1,4-dihydro-2,6-dimethyl-4-(5-nitrothienyl)-5-(5-benzyl-1,2,4-oxadiazol-3-yl)pyridine-3-carboxylate, melting point=201° to 203° C.;

(l) 2-Methoxypropyl 1,4-dihydro-2,6-dimethyl-4-(2-nitrophenyl)-5-(3-methyl-1,2,4-thiadiazol-5-yl)pyridine-3-carboxylate, melting point=185° to 188° C.;

(m) n-Butyl 1,4-dihydro-2,6-dimethyl-4-(3-cyanophenyl)-5-(3-methylthio-1,2,4-thiadiazol-5-yl)pyridine-3-carboxylate, melting point=170° to 172° C.;

(n) Isopropyl 1,4-dihydro-2,6-dimethyl-4-(3-nitrophenyl)-5-(1,3,4-oxadiazol-2-yl)pyridine-3-carboxylate, melting point=190° to 192° C.;

(o) 2-Methoxyethyl 1,4-dihydro-2,6-dimethyl-4-(2-nitrophenyl)-5-(1,3,4-oxadiazol-2-yl)pyridine-3-carboxylate, melting point=168° to 170° C.;

(p) 2-Methoxyethyl 1,4-dihydro-2,6-dimethyl-4-(2,3-dichlorophenyl)-5-(1,3,4-oxadiazol-2-yl)pyridine-3-carboxylate, melting point=173° to 175° C.;

(q) Neopentyl 1,4-dihydro-2,6-dimethyl-4-(3-nitrophenyl)-5-(1,3,4-oxadiazol-2-yl)pyridine-3-carboxylate, melting point=196° to 198° C.;

(r) Methyl 1,4-dihydro-2,6-dimethyl-4-(3-nitrophenyl)-5-(3-benzyl-1,2,4-oxadiazol-5-yl)pyridine-3-carboxylate, melting point=145° to 147° C.;

(s) Methyl 1,4-dihydro-2,6-dimethyl-4-(2,3-dichlorophenyl)-5-(3-benzyl-1,2,4-oxadiazol-5-yl)pyridine-3-carboxylate, melting point=205° to 207° C.;

(t) Methyl 1,4-dihydro-2,6-dimethyl-4-(2-nitrophenyl)-5-(3-benzyl-1,2,4-oxadiazol-5-yl)pyridine-3-carboxylate, melting point=189° to 191° C.;

(u) Methyl-1,4-dihydro-2,6-dimethyl-4-(3-dihydrofluoromethylphenyl)-5-(3-benzyl-1,2,4-oxadiazol-5-yl)pyridine-3-carboxylate, melting point=179° to 181° C.;

(v) 2-Methoxyethyl 1,4-dihydro-2,6-dimethyl-4-(3-nitrophenyl)-5-(3-benzyl-1,2,4-oxadiazol-5-yl)pyridine-3-carboxylate, melting point=108° to 111° C.;

(w) Methyl 1,4-dihydro-2,6-dimethyl-4-(2-chlorophenyl)-5-(3-benzyl-1,2,4-oxadiazol-5-yl)pyridine-3-carboxylate, melting point=143° to 145° C.;

(x) 1,4-Dihydro-2,6-dimethyl-4-(3-nitrophenyl)-5-(3-benzyl-1,2,4-oxadiazol-5-yl)pyridine-3-carbonitrile, melting point=238° to 240° C.;

(y) 2-Methoxyethyl 1,4-dihydro-2,6-dimethyl-4-(2,3-dichlorophenyl)-5-(3-benzyl-1,2,4-oxadiazol-5-yl)pyridine-3-carboxylate, melting point=101° to 103° C.;

(z) Isopropyl 1,4-dihydro-2,6-dimethyl-4-(3-pyridyl)-5-(3-benzyl-1,2,4-oxadiazol-5-yl)pyridine-3-carboxylate, melting point=157° to 160° C.;

(z1) 2-Isopropoxyethyl 1,4-dihydro-2,6-dimethyl-4-(2,3-dichlorophenyl)-5-(2-methyl-1,3,4-oxadiazol-5-yl)pyridine-3-carboxylate, melting point=163° to 165° C.;

(z2) Isopropyl 1,4-dihydro-2,6-dimethyl-4-(2,3-dichlorophenyl)-5-(1,3,4-oxadiazol-2-yl)pyridine-3-carboxylate, melting point=166° to 168° C.;

EXAMPLE 3

1,4-Dihydro-2,6-dimethyl-3,5-di(3-methyl-1,2,4-oxadiazol-5-yl)-4-(2,3-dichlorophenyl)pyridine 1.75 g of 2,3-dichlorobenzaldehyde, 2.8 g of 3-methyl-5-acetonyl-1,2,4-oxadiazole and 1.2 g of 25% strength aqueous ammonia solution in 50 ml of ethanol are heated to boiling overnight. The solid which precipitates after cooling to 0° C. is filtered off with suction and recrystallised from ethanol. Melting point=255° to 256° C.;

| Analysis: | C | H | N | O | Cl |
|---|---|---|---|---|---|
| Calculated: | 54.6 | 4.1 | 16.7 | 7.7 | 17.0 |
| Found: | 54.5 | 4.2 | 16.4 | 7.9 | 17.0 |

The following are prepared in a similar manner:

(a) 1,4-Dihydro-2,6-dimethyl-3,5-di(1,3,4-oxadiazol-2-yl)-4-(3-nitrophenyl)pyridine, melting point=254° to 256° C.;

(b) 1,4-Dihydro-2,6-dimethyl-3,5-di(5-methyl-1,2,4-oxadiazol-3-yl)-4-(p-tolyl)pyridine, melting point=304° to 306° C.;

(c) 1,4-Dihydro-2,6-dimethyl-3,5-di(3-methyl-1,2,4-thiadiazol-5-yl)-4-(2,3-dichlorophenyl)pyridine, melting point=231° to 233° C.;

(d) 1,4-Dihydro-2,6-dimethyl-3,5-di(5-methoxymethyl-1,2,4-oxadiazol-3-yl)-4-(2-trifluoromethylphenyl)-pyridine, melting point=196° to 198° C.;

(e) 1,4-Dihydro-2,6-dimethyl-3,5-di(3-benzyl-1,2,4-oxadiazol-5-yl)-4-(2-pyridinyl)pyridine, melting point=248° to 249° C.;

(f) 1,4-Dihydro-2,6-dimethyl-3,5-di(4-methyl-5-ethoxycarbonyl-1,3-thiazol-2-yl)-4-(3-nitrophenyl)pyridine, melting point=227° to 229° C.:

EXAMPLE 4

2-Methoxyethyl 1,4-dihydro-2,6-dimethyl-4-(3,5-dichlorophenyl)-5-(3-ethyl-1,2,4-oxadiazol-5-yl)pyridine-3-carboxylate 0.93 g of 3-ethyl-5-acetonyl-1,2,4-oxadiazole, 0.96 g of methoxyethyl β-aminocrotonate and 0.95 g of 3,5-dichlorobenzaldehyde in 30 ml of isopropanol are heated to reflux for 8 hours. After concentrating, the oily residue is triturated with diethyl ether, whereupon crystallisation gradually occurs. The solid is filtered off with suction and recrystallised from isopropanol. Yield: 1.7 g; melting point: 178° to 180° C.

| Analysis: | C | H | N | O | Cl |
|---|---|---|---|---|---|
| Calculated: | 55.9 | 4.9 | 9.3 | 14.2 | 15.7 |
| Found: | 56.1 | 5.1 | 9.1 | 14.0 | 15.5 |

The following are prepared in a similar manner:

(a) 2-Methoxyethyl 1,4-dihydro-2,6-dimethyl-4-(3-nitrophenyl)-5-(3-ethyl-1,2,4-oxadiazol-5-yl)pyridine-3-carboxylate, melting point=206° to 208° C.;

(b) 2-Methoxyethyl 1,4-dihydro-2,6-dimethyl-4-(2,3-dichlorophenyl)-5-(3-ethyl-1,2,4-oxadiazol-5-yl)pyridine-3-carboxylate, melting point=153° to 155° C.;

(c) Methyl 1,4-dihydro-2,6-dimethyl-4-(2,3-dichlorophenyl)-5-(3-ethyl-1,2,4-oxadiazol-5-yl)pyridine-3-carboxylate, melting point=190° to 192° C.;

(d) 2-Methoxyethyl 1,4-dihydro-2,6-dimethyl-4-(4-nitrophenyl)-5-(3-ethyl-1,2,4-oxadiazol-5-yl)pyridine-3-carboxylate, melting point=171° to 173° C.;

(e) 2-Methoxyethyl 1,4-dihydro-2,6-dimethyl-4-(2,4-dichlorophenyl)-5-(3-ethyl-1,2,4-oxadiazol-5-yl)pyridine-3-carboxylate, melting point=165° to 167° C.;

(f) 2-Methoxyethyl 1,4-dihydro-2,6-dimethyl-4-(3,4-dichlorophenyl)-5-(3-ethyl-1,2,4-oxadiazol-5-yl)pyridine-3-carboxylate, melting point=178° to 180° C.;

(g) 2-Methoxyethyl 1,4-dihydro-2,6-dimethyl-4-(3-bromophenyl)-5-(3-ethyl-1,2,4-oxadiazol-5-yl)pyridine-3-carboxylate, melting point=184° to 186° C.;

(h) 2-Methoxyethyl 1,4-dihydro-2,6-dimethyl-4-(2,5-dimethylphenyl)-5-(3-ethyl-1,2,4-oxadiazol-5-yl)pyridine-3-carboxylate, melting point=157° to 159° C.;

(i) 2-Methoxyethyl 1,4-dihydro-2,6-dimethyl-4-(2-chloro-6-nitrophenyl)-5-(3-ethyl-1,2,4-oxadiazol-5-yl)pyridine-3-carboxylate, melting point=162° to 164° C.;

(k) 2-Methoxyethyl 1,4-dihydro-2,6-dimethyl-4-(3-nitrophenyl)-5-(2-ethyl-1,3,4-oxadiazol-5-yl)pyridine-3-carboxylate, melting point=224° to 226° C.;

(l) Methyl 1,4-dihydro-2,6-dimethyl-4-(3-nitrophenyl)-5-(2-ethyl-1,3,4-oxadiazol-5-yl)pyridine-3-carboxylate, melting point=236° to 238° C.;

(m) 2-Methoxyethyl 1,4-dihydro-2,6-dimethyl-4-(2,3-dichlorophenyl)-5-(2-ethyl-1,3,4-oxadiazol-5-yl)pyridine-3-carboxylate, melting point=166° to 168° C.;

(n) Isobutyl 1,4-dihydro-2,6-dimethyl-4-(3-nitrophenyl)-5-(2-ethyl-1,3,4-oxadiazol-5-yl)pyridine-3-carboxylate, melting point=204° to 206° C.;

(o) 2-(N-Benzyl-N-methylamino)ethyl 1,4-dihydro-2,6-dimethyl-4-(3-nitrophenyl)-5-(1,3,4-oxadiazol-2-yl)pyridine-3-carboxylate, melting point=166° to 168° C.;

(p) Isobutyl 1,4-dihydro-2,6-dimethyl-4-(3-nitrophenyl)-5-(3-benzyl-1,2,4-oxadiazol-5-yl)pyridine-3-carboxylate, melting point=121° to 124° C.;

(q) Tert.-butyl 1,4-dihydro-2,6-dimethyl-4-(3-nitrophenyl)-5-(3-benzyl-1,2,4-oxadiazol-5-yl)pyridine-3-carboxylate, melting point=131° to 133° C.;

(r) Cyclohexyl 1,4-dihydro-2,6-dimethyl-4-(3-nitrophenyl)-5-(5-i-propylthio-1,3,4-oxadiazol-2-yl)pyridine-3-carboxylate, melting point=189° to 191° C.;

(s) Cyclopentyl 1,4-dihydro-2,6-dimethyl-4-(3-nitrophenyl)-5-(5-cyclohexyl-1,2,4-oxadiazol-3-yl)pyridine-3-carboxylate, melting point=201° to 202° C.

EXAMPLE 5

Methyl 1,4-dihydro-2,6-dimethyl-4-(3-nitrophenyl)-5-(4-methyl-5-ethoxycarbonyl-2-thiazolyl)pyridine-3-carboxylate (A) 2.3 g of 2-(2-aminopropen-1-yl)-4-methyl-5-ethoxycarbonyl-thiazole, 1.5 g of 3-nitrobenzaldehyde and 1.2 g of methyl acetoacetate in 30 ml of ethanol are heated to reflux for 3 hours. Petroleum ether is added to the cooled mixture which is then stirred overnight at room temperature, whereupon a precipitate separates out; this is recrystallised from ethanol. Yield: 1.8 g; melting point=203° to 205° C.

| Analysis: | C | H | O | N | S |
|---|---|---|---|---|---|
| Calculated: | 59.6 | 5.2 | 21.7 | 6.3 | 7.2 |
| Found: | 59.5 | 5.1 | 21.9 | 6.2 | 7.3 |

(B) The 2-(2-aminopropen-1-yl)-4-methyl-5-ethoxycarbonylthiazole required as starting product is prepared as follows: 34.8 g of aminocrotonic thioamide, 49.5 g of 2-chloroacetoacetic ester and 45 ml of triethylamine in 150 ml of ethanol are heated to reflux for 20 minutes. The mixture is then allowed to cool to room temperature and the mixture is diluted with water, whereupon a precipitate separates out. This is filtered off with suction and recrystallised from i-propanol. Yield: 38.3 g; melting point=98° to 100° C.

| Analysis: | C | H | N | O | S |
|---|---|---|---|---|---|
| Calculated: | 53.1 | 6.2 | 12.4 | 14.2 | 14.2 |
| Found: | 52.9 | 6.0 | 12.2 | 14.4 | 14.4 |

The following are prepared in a similar manner:

(a) Isopropyl 1,4-dihydro-2,6-dimethyl-4-(2,3-dichlorophenyl)-5-(4-methyl-5-ethoxycarbonyl-2-thiazolyl)-pyridine-3-carboxylate, melting point=168° to 170° C.;

(b) 2-Methoxyethyl 1,4-dihydro-2,6-dimethyl-4-(3-nitrophenyl)-5-(4-methyl-5-ethoxycarbonyl-2-thiazolyl)pyridine-3-carboxylate, melting point=150° to 152° C.;

(c) 2-(N-Benzyl-N-methylamino)ethyl 1,4-dihydro-2,6-dimethyl-4-(3-nitrophenyl)-5-(4-methyl-5-ethoxycarbonyl-2-thiazolyl)pyridine-3-carboxylate, melting point=148° to 150° C.;

(d) Methyl 1,4-dihydro-2,6-dimethyl-4-(3-nitrophenyl)-5-(4-phenyl-2-thiazolyl)pyridine-3-carboxylate, melting point=212° to 215° C.

EXAMPLE 6

Sec.-butyl 1,4-dihydro-2,6-dimethyl-4-(2,3-dichlorophenyl)-5-(3-benzyl-1,2,4-oxadiazol-5-yl)pyridine-3-carboxylate 1.75 g of 2,3-dichlorobenzaldehyde, 2.2 g of 3-acetonyl-1,2,4-oxadiazole, 1.6 g of sec.-butyl acetoacetate and 1.2 g of 25% strength aqueous ammonia solution in 50 ml of ethanol are heating to boiling for 6 hours. After concentrating, there remains an oily residue which is triturated with ether/petroleum ether and gradually crystallises. The resulting solid is then recrystallised from ethyl acetate/isopropanol: melting point=116° to 117° C.

| Analysis: | C | H | N | O | Cl |
|---|---|---|---|---|---|
| Calculated: | 63.3 | 5.3 | 8.2 | 9.4 | 13.9 |
| Found: | 63.1 | 5.4 | 8.1 | 9.6 | 13.7 |

EXAMPLE 7

Methyl 1,4-dihydro-2,6-dimethyl-4-(2-nitrophenyl)-5-(4-methyl-5-ethoxycarbonyl-2-thiazolyl)pyridine-3-carboxylate 2.3 g of 2-(2-amino-1-propenyl)-4-methyl-5-ethoxycarbonylthiazole and 2.5 g of methyl 2-nitrobenzylideneacetoacetate in isopropanol are heated to boiling for 4 hours. On allowing to cool overnight, a precipitate separates out and is recrystallised from ethanol. Melting point=191° to 192° C.

| Analysis: | C | H | N | O | S |
|---|---|---|---|---|---|
| Calculated: | 59.6 | 5.2 | 6.3 | 21.7 | 7.2 |
| Found: | 59.4 | 5.3 | 6.2 | 21.9 | 7.1 |

Pharmaceutical products are described in the examples which follow:

EXAMPLE 8

Soft gelatin capsules containing 5 mg of active compound per capsule

| | per capsule |
|---|---|
| Methyl 1,4-dihydro-2,6-dimethyl-4-(3-nitrophenyl)-5-(3-methyl-1,2,4-oxadiazol-5-yl)pyridine-3-carboxylate | 5 mg |
| Mixture of triglycerides fractionated from coconut fat | 150 mg |
| Contents of capsule | 155 mg |

EXAMPLE 9

Solution for injection containing 1 mg of active compound per ml

| | per ml |
|---|---|
| Methyl 1,4-dihydro-2,6-dimethyl-4-(3-nitrophenyl)-5-(3-methyl-1,2,4-oxadiazol-5-yl)pyridine-3-carboxylate | 1.0 mg |
| Polyethylene glycol 400 | 0.3 ml |
| Sodium chloride | 2.7 mg |
| Water for injection ad 1.0 | ml |

EXAMPLE 10

Emulsion containing 10 mg of active compound per 5 ml

| | per 100 ml |
|---|---|
| 2-Methoxyethyl 1,4-dihydro-2,6-dimethyl-4-(3-nitrophenyl)-5-(1,3,4-oxadiazol-2-yl)pyridine-3-carboxylate | 0.2 g |
| Neutral oil q.s. | |
| Sodium carboxymethylcellulose | 0.6 g |
| Polyoxyethylene stearate q.s. | |
| Glycerol, pure | 0.2 to 2.0 g |
| Flavouring q.s. | |
| Water (deionised or distilled) ad | 100 ml |

EXAMPLE 11

Rectal formulation containing 8 mg of active compound per suppository

| | per suppository |
|---|---|
| 2-Methoxyethyl 1,4-dihydro-2,6-dimethyl-4-(3-nitrophenyl)-5-(1,3,4-oxadiazol-2-yl)pyridine-3-carboxylate | 8 mg |
| Suppository base | ad 2 g |

EXAMPLE 12

Tablets containing 5 mg of active compound per tablet

| | per tablet |
|---|---|
| 1,4-Dihydro-2,6-dimethyl-3,5-di(3-methyl-1,2,4-oxadiazol-5-yl)-4-(2,3-dichlorophenyl)pyridine | 5 mg |
| Maize starch (white) | 150 mg |
| Lactose | 60 mg |
| Microcrystalline cellulose | 50 mg |
| Polyvinylpyrrolidone | 20 mg |
| Magnesium stearate | 2 mg |
| Sodium carboxymethyl starch | 25 mg |
| | 312 mg |

EXAMPLE 13

Coated tablets containing an active compound according to the invention and another therapeutically active substance

| | per coated tablet |
|---|---|
| Methyl 1,4-dihydro-2,6-dimethyl-4-(3-nitrophenyl)-5-(3-methyl-1,2,4-oxadiazol-5-yl)pyridine-3-carboxylate | 6 mg |
| Propranolol | 40 mg |
| Lactose | 90 mg |
| Maize starch | 90 mg |
| Sec.-calcium phosphate | 34 mg |
| Soluble starch | 3 mg |
| Magnesium stearate | 3 mg |
| Colloidal silica | 4 mg |
| | 270 mg |

EXAMPLE 14

Coated tablets containing an active compound according to the invention and another therapeutically active substance

| | per coated tablet |
|---|---|
| Methyl 1,4-dihydro-2,6-dimethyl-4-(3-nitrophenyl)-5-(3-methyl-1,2,4-oxadiazol-5-yl)pyridine-3-carboxylate | 6 mg |
| Molsidomine | 5 mg |
| Lactose | 90 mg |
| Maize starch | 90 mg |
| Sec.-calcium phosphate | 34 mg |
| Soluble starch | 3 mg |
| Magnesium stearate | 3 mg |
| Colloidal silica | 4 mg |
| | 235 mg |

EXAMPLE 15

Capsules containing an active compound according to the invention and another therapeutically active substance

| | per capsule |
|---|---|
| 2-Methoxyethyl 1,4-dihydro-2,6-dimethyl-4-(3-nitrophenyl)-5-(1,3,4-oxadiazol-2-yl)pyridine-3-carboxylate | 70 mg |
| Prazosin | 5 mg |
| Maize starch | 185 mg |
| | 200 mg |

The calcium-antagonistic action of the compounds of the formula I has been determined using a modification of the method of Godfraind and Kaba (Arch. Int. Pharmacodyn. Ther. 196, (Suppl.) 35 to 49, 1972) and of Schümann et al (Naunyn-Schmiedeberg's Arch. Pharmacol. 289, 409 to 418, 1975). This entailed helical strips of pulmonary artery of guinea pigs being equilibrated in calcium-free Tyrode's solution and depolarised with 40 mmol of potassium. Addition of 0.5 mmol of $CaCl_2$ then initiates contraction. The relaxant action of the test substance is determined by cumulative addition of concentrations increasing in steps of ½ log 10. The concentration of the test substance which inhibits contraction by 50% (=$IC_{50}$, mol/l) is determined from the concentration-effect curve (abscissa: -log mol/l of test substance, ordinate: % inhibition of the maximum contraction, mean value from 4 to 6 strips of vessel). The $IC_{50}$ values thus obtained are reported in the table which follows. As comparison with the $IC_{50}$ value for the known compound nifedipine (=dimethyl 1,4-dihydro-2,6-dimethyl-4-(2-nitrophenyl)pyridine-3,5-dicarboxylate), which is $3 \times 10^{-9}$ (compare German Patent B 16 70 827) shows, the values for some of the compounds of the formula I are considerably more advantageous.

TABLE

| Compound of the formula I according to Example | $IC_{50}$(mol/l) |
|---|---|
| 1t | $1.5 \times 10^{-9}$ |
| 1z | $1.5 \times 10^{-10}$ |
| 2b | $4 \times 10^{-10}$ |
| 2e | $1.6 \times 10^{-9}$ |
| 2n | $9 \times 10^{-11}$ |
| 2o | $3 \times 10^{-10}$ |
| 2r | $5 \times 10^{-10}$ |
| 2s | $7 \times 10^{-10}$ |
| 2t | $1 \times 10^{-9}$ |
| 2v | $7 \times 10^{-10}$ |
| 2w | $2.5 \times 10^{-9}$ |
| 2z1 | $1.5 \times 10^{-9}$ |
| 2z2 | $2 \times 10^{-10}$ |
| 3a | $2 \times 10^{-9}$ |
| 4b | $1.8 \times 10^{-9}$ |
| 4c | $2.4 \times 10^{-9}$ |
| 4k | $1 \times 10^{-9}$ |
| 4m | $1.5 \times 10^{-9}$ |
| 5b | $1.6 \times 10^{-9}$ |

We claim:

1. A substituted 1,4-dihydropyridine of formula I

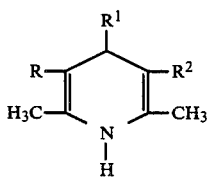

in which

R denotes —$CO_2R^3$, cyano or one of the meanings indicated under $R^2$;

$R^1$ denotes phenyl, optionally having 1 or 2 identical or different substituents selected from the group consisting of alkyl having from 1 to 4C atoms, alkoxy having from 1 to 4C atoms, halogen, trifluoromethyl, nitro or cyano;

$R^2$ denotes oxadiazolyl or thiadiazolyl each 5-membered ring optionally having 1 substituent selected from the group consisting of alkyl having from 1 to 4C atoms, alkylthio having from 1 to 4C atoms, aralkyl having a total of from 7 to 9C atoms, alkoxyalkyl having a total of from 2 to 5C atoms, cycloalkyl having 5 or 6C atoms, aminocarbonylmethylthio, methoxycarbonyl, ethoxycarbonyl and phenyl;

$R^3$ denotes alkyl having from 1 to 6C atoms, alkoxyalkyl having from 3 to 8C atoms, dialkylaminoalkyl having a total of from 4 to 9 C atoms, N-aralkyl-N-alkylaminoalkyl having a total of from 10 to 14C atoms or cycloalkyl having 5 or 6C atoms;

or an acid-addition salt thereof.

2. A substituted 1,4-dihydropyridine according to claim 1, wherein R denotes —$CO_2R^3$, and $R^3$ denotes alkyl having from 1 to 5C atoms, alkoxyalkyl having from 1 to 4C atoms in the alkoxy moiety and from 2 to 4C atoms in the alkyl moiety, or dialkylaminoalkyl having a total of from 3 to 6 C atoms, each of the alkyl groups substituting the amino group having from 1 to 3C atoms.

3. A substituted 1,4-dihydropyridine according to claim 1, wherein $R^1$ denotes phenyl which optionally has 1 or 2 identical or different substituents selected from the group consisting of chlorine, bromine, fluorine, nitro, cyano, methyl, methoxy and trifluoromethyl.

4. A substituted 1,4-dihydropyridine according to claim 1, wherein $R^2$ represents oxadiazolyl or an oxadiazolyl which is substituted by methyl, ethyl, i-propyl, tert.-butyl, benzyl, methylthio, i-propylthio, aminocarbonylthio or methoxymethyl.

5. A substituted 1,4-dihydropyridine according to claim 1, wherein $R^2$ denotes 1,3,4-oxadiazol-2-yl, 5-methyl-1,3,4-oxadiazol-2-yl, 5-ethyl-1,3,4-oxadiazol-2-yl, 3-methyl-1,2,4-oxadiazol-5-yl, 3-ethyl-1,2,4-oxadiazol-5-yl or 3-benzyl-1,2,4-oxadiazol-5-yl or 3-benzyl-1,2,4-oxadiazol-5-yl.

6. A substituted 1,4-dihydropyridine according to claim 1, wherein $R^1$ denotes 2-nitrophenyl, 3-nitrophenyl, 3-cyanophenyl, 2-chlorophenyl or 2,3-dichlorophenyl.

7. A substituted 1,4-dihydropyridine according to claim 1 wherein R denotes —$CO_2R^3$, and $R^3$ denotes methyl, n-propyl, i-propyl, n-butyl, i-butyl, tert.-butyl, 2-methoxyethyl or 2-(i-propoxy)ethyl.

8. A substituted 1,4-dihydropyridine of formula I

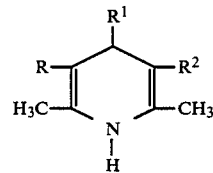

in which

R denotes —$CO_2R^3$;

$R^1$ denotes phenyl which optionally has 1 or 2 identical or different substituents selected from the group consisting of chlorine, bromine, fluorine, nitro, cyano, methyl, methoxy and trifluoromethyl;

$R^2$ denotes oxadiazolyl or an oxadiazolyl which is substituted by methyl, ethyl, i-propyl, tert.-butyl, benzyl, methylthio, i-propylthio, aminocarbonylthio or methoxymethyl; and $R^3$ denotes alkyl having from 1 to 5C atoms, alkoxyalkyl having from 1 to 4C atoms in the alkoxy moiety and from 2 to 4C atoms in the alkyl moiety, or dialkylaminoalkyl having a total of from 3 to 6C atoms, each of the alkyl groups substituting the amino group having from 1 to 3C atoms;

or an acid-addition salt thereof.

9. A substituted 1,4-dihydropyridine according to claim 8, wherein $R^2$ denotes 1,3,4-oxadiazol-2-yl, 5-methyl-1,3,4-oxadiazol-2-yl, 5-ethyl-1,3,4-oxadiazol-2-yl, 3-methyl-1,2,4-oxadiazol-5-yl, 3-ethyl-1,2,4-oxadiazol-5-yl or 3-benzyl-1,2,4-oxadiazol-5-yl.

10. A substituted 1,4-dihydropyridine according to claim 8, wherein $R^1$ denotes 2-nitrophenyl, 3-nitrophenyl, 3-cyanophenyl, 2-chlorophenyl or 2,3-dichlorophenyl.

11. A substituted 1,4-dihydropyridine according to claim 10, wherein $R^3$ denotes methyl, n-propyl, i-propyl, n-butyl, i-butyl, tert.-butyl, 2-methoxyethyl or 2-(i-propoxy)-ethyl.

12. A substituted 1,4-dihydropyridine of formula I

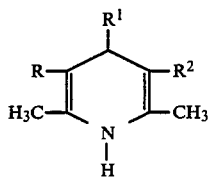

(I)

in which

R denotes —$CO_2R^3$; $R^1$ denotes 2-nitrophenyl, 3-nitrophenyl, 3-cyanophenyl, 2-chlorophenyl or 2,3-dichlorophenyl;

$R^2$ denotes 1,3,4-oxadiazol-2-yl, 5-methyl-1,3,4-oxadiazol-2-yl, 5-ethyl-1,3,4-oxadiazol-2-yl, 3-methyl-1,2,4-oxadiazol-5-yl, 3-ethyl-1,2,4-oxadiazol-5-yl or 3-benzyl-1,2,4-oxadiazol-5-yl; and $R^3$ denotes methyl, n-propyl, i-propyl, n-butyl, i-butyl, tert.-butyl, 2-methoxyethyl or 2-(i-propoxy)ethyl.

13. Isobutyl 1,4-dihydro-2,6-dimethyl-4-(3-nitrophenyl)-5-(1,3,4-oxadiazol-2-yl)pyridine-3-carboxylate.

14. Methyl 1,4-dihydro-2,6-dimethyl-4-(2,3-dichlorophenyl)-5-(1,3,4-oxadiazol-2-yl)pyridine-3-carboxylate.

15. Methyl 1,4-dihydro-2,6-dimethyl-4-(3-nitrophenyl)-5-(3-benzyl-1,2,4-oxadiazol-5-yl)pyridine-3-carboxylate.

16. Methyl 1,4-dihydro-2,6-dimethyl-4-(2,3-dichlorophenyl)-5-(3-benzyl-1,2,4-oxadiazol-5-yl)pyridine-3-carboxylate.

17. 2-Methoxyethyl 1,4-dihydro-2,6-dimethyl-4-(3-nitrophenyl)-5-(3-benzyl-1,2,4-oxadiazol-5-yl)pyridine-3-carboxylate.

18. Isopropyl 1,4-dihydro-2,6-dimethyl-4-(3-nitrophenyl)-5-(1,3,4-oxadiazol-2-yl)pyridine-3-carboxylate.

19. Isopropyl 1,4-dihydro-2,6-dimethyl-4-(2,3-dichlorophenyl)-5-(1,3,4-oxadiazol-2-yl)pyridine-3-carboxylate.

20. A substituted 1,4-dihydropyridine according to claim 1 wherein R denotes —$CO_2R^3$ or cyano.

21. A substituted 1,4-dihydropyridine according to claim 1 wherein R is an optionally-substituted oxadiazolyl or thiadiazolyl ring.

22. A substituted 1,4-dihydropyridine according to claim 21 wherein $R^1$ is optionally-substituted phenyl.

23. A substituted 1,4-dihydropyridine of claim 1, formula 1

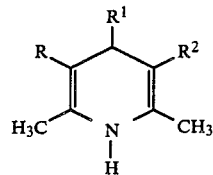

in which

R denotes —$CO_2R^3$ or cyano; $R^1$ denotes phenyl which has optionally 1 or 2 identical or different substituents selected from the group consisting of alkyl having from 1 to 4C atoms, alkoxy having from 1 to 4C atoms, chlorine, bromine, fluorine, trifluoromethyl, nitro or cyano;

$R^2$ denotes oxadiazolyl or thiadiazolyl or an oxadiazolyl or thiadiazolyl having 1 substituent selected from the group consisting of alkyl having from 1 to 4C atoms, alkylthio having from 1 to 4C atoms, benzyl, alkoxyalkyl having a total of from 2 to 5C atoms, cycloalkyl having 5 or 6C atoms or aminocarbonylmethylthio;

$R^3$ denotes alkyl having from 1 to 6C atoms, alkoxyalkyl having from 3 to 8C atoms, dialkylaminoalkyl having a total of from 4 to 9C atoms, N-aralkyl-N-alkylaminoalkyl having a total of from 10 to 14C atoms or cycloalkyl having 5 or 6C atoms; or an acid-addition salt thereof.

24. A pharmaceutical product useful for controlling and/or preventing angina pectoris, high blood pressure, and/or disturbances of cerebral and peripherel blood flow and having, as active component, from about 0.5 to 90 percent by weight of a compound of claim 1 or of a pharmaceutically-acceptable acid-addition salt thereof, together with a pharmaceutically-acceptable vehicle and, optionally, a pharmaceutically-acceptable additive.

25. A process of administering an effective calcium antagonist amount of a pharmacologically-active substituted 1,4-dihydropyridine of claim 1, or of a pharmaceutically-acceptable acid-addition salt thereof, to a host.

26. A process for controlling or preventing angina pectoris, high blood pressure and disturbances of cerebral and peripheral blood flow which comprises administering an effective amount of a pharmacologically-active substituted 1,4-dihydropyridine of claim 1, or of a pharmacologically-acceptable acid-addition salt thereof, to a host which is subject to or afflicted with one or more of these conditions.

* * * * *

UNITED STATES PATENT AND TRADEMARK OFFICE
CERTIFICATE OF CORRECTION

PATENT NO. : 4,558,058
DATED : December 10, 1985
INVENTOR(S) : SCHÖNAFINGER et al It is certified that error appears in the above-identified patent and that said Letters Patent are hereby corrected as shown below:

Column 10, line 4, "dimethyl-(2,3-" should read

--dimethyl-4-(2,3- --.

Column 11, lines 32 and 33, "dihydrofluoromethylphenyl" should read --trifluoromethylphenyl--.

Signed and Sealed this

Second Day of September 1986

[SEAL]

Attest:

Attesting Officer

DONALD J. QUIGG

Commissioner of Patents and Trademarks